United States Patent
Goetzl

(10) Patent No.: US 9,958,460 B2
(45) Date of Patent: *May 1, 2018

(54) BIOMARKERS AND DIAGNOSTIC METHODS FOR ALZHEIMER'S DISEASE AND OTHER NEURODEGENERATIVE DISORDERS

(71) Applicant: NANOSOMIX, INC., Aliso Viejo, CA (US)

(72) Inventor: Edward J. Goetzl, San Francisco, CA (US)

(73) Assignee: NANOSOMIX, INC., Aliso Viejo, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/522,585

(22) Filed: Oct. 24, 2014

(65) Prior Publication Data

US 2015/0119278 A1   Apr. 30, 2015

Related U.S. Application Data

(60) Provisional application No. 61/895,376, filed on Oct. 24, 2013, provisional application No. 61/978,994, filed on Apr. 14, 2014, provisional application No. 62/047,062, filed on Sep. 8, 2014.

(51) Int. Cl.
*G01N 33/53*  (2006.01)
*G01N 33/567*  (2006.01)
*G01N 33/68*  (2006.01)

(52) U.S. Cl.
CPC ... *G01N 33/6896* (2013.01); *G01N 2800/285* (2013.01); *G01N 2800/2814* (2013.01); *G01N 2800/2821* (2013.01); *G01N 2800/2835* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| 2007/0172900 A1 | 7/2007 | Cahill et al. |
| 2008/0220449 A1 | 9/2008 | Vasan et al. |
| 2012/0164628 A1* | 6/2012 | Duffin .............. G01N 33/54366 435/5 |
| 2013/0178383 A1 | 7/2013 | Spetzler et al. |

FOREIGN PATENT DOCUMENTS

| WO | WO 2011/094645 A1 | 8/2011 |
| WO | WO 2013/071239 A1 | 5/2013 |

OTHER PUBLICATIONS

Vega et al., 2005, Mol. Brain Res., 138:135-44.*
Samon et al., J. Biol. Chem., 2012, 287(6):3842-9.*
Plouffe et al., PLos One, 2012, 7(5), e36873.*
Zetterberg et al., Plasma Tau Levels in Alzheimer's Disease, Alzhiemers Res Ther., 2013, 5(2):9.
International Search Report and the Written Opinion of the International Searching Authority re PCT/US2014/62074.
Third Party Observation re PCT/US2014/062074.
Liu et al., Heterogeneity of Tau Proteins in Alzheimer's Disease, Am J Pathol., 1993, 142 387-94.
Huang and Jiang, Accumulated Amyloid-β Peptide and Hyperphosphorylated Tau Protein: Relationship and Links in Alzheimer's Disease, Journal of Alzheimer's Disease, 2009, 15-27.
Ou et al., Heat Shock Protein 90 in Alzheimer's Disease, Biomed Res Int., 2014, 796869.
Schlering et al., CSF neurofilament concentration reflects disease severity in frontotemporal degeneration, Ann Neurol., 2014, 75 116-26.

* cited by examiner

*Primary Examiner* — Olga N Chernyshev
(74) *Attorney, Agent, or Firm* — Law Office of Christopher Jacob, P.C.

(57) ABSTRACT

The present invention relates to biomarkers and diagnostic and prognostic methods for Alzheimer's disease and other neurodegenerative disorders. The invention also provides compositions for detecting the biomarker as well as compositions and methods useful for treating Alzheimer's disease and other neurodegenerative disorders.

6 Claims, No Drawings

BIOMARKERS AND DIAGNOSTIC METHODS FOR ALZHEIMER'S DISEASE AND OTHER NEURODEGENERATIVE DISORDERS

RELATED APPLICATIONS

This application claims priority to the U.S. Provisional Patent Application Ser. No. 61/895,376, filed on Oct. 24, 2013, U.S. Provisional Patent Application Ser. No. 61/978,994, filed on Apr. 14, 2014, and U.S. Provisional Patent Application Ser. No. 62/047,062, filed on Sep. 8, 2014, which are hereby incorporated by reference herein in their entirety.

FIELD OF THE INVENTION

The present invention relates to biomarkers and diagnostic and prognostic methods for Alzheimer's disease and other neurodegenerative disorders. The invention also provides compositions for detecting the biomarker as well as compositions and methods useful for treating Alzheimer's disease and other neurodegenerative disorders.

BACKGROUND OF THE INVENTION

More than 5.4 million Americans and 35 million people worldwide have Alzheimer's disease, the most common form of dementia. Currently, the only definitive way to diagnose Alzheimer's disease is by direct examination of brain tissue after a patient dies. Doctors use brain imaging, evaluation of behavior, psychiatric tests, and other means to diagnose the disease in the patients suspected of having Alzheimer's disease, but none are highly accurate, and many are costly or not practical.

Therefore, there is a need in the art for biomarkers and methods for diagnosing Alzheimer's disease and other neurodegenerative disorders. Additionally, there is a need in the art for compositions for detecting the biomarkers as well as compositions and methods useful for treating Alzheimer's disease and other neurodegenerative disorders. The present invention meets this need by providing accurate, noninvasive methods for diagnosing Alzheimer's disease and other neurodegenerative disorders. The present invention further provides novel methods, assays, kits, and compositions for diagnosing, prognosing, predicting, and treating Alzheimer's disease and other neurodegenerative disorders.

SUMMARY OF THE INVENTION

The present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: assaying the level of one or more biomarkers in a biological sample from the subject; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the biomarker, wherein at least one of the one or more biomarkers are selected from the group consisting of Tau, phosphorylated Tau, Aβ1-42, TDP-43, α-synuclein, SOD-1, FUS, FKBP51, IRS-1, phosphorylated IRS-1, cathepsin D (CTSD), type 1 lysosome-associated membrane protein (LAMP1), ubiquitinylated proteins (UBP), heat-shock protein 70 (HSP70), neuron-specific enolase (NSE), neurofilament light chain (NFL), CD9, CD63, CD81, and CD171. In some embodiments, the level of the one or more biomarkers in the biological sample is compared to the level of one or more biomarkers in a control sample and wherein the level of the one or more biomarkers of the biological sample is elevated compared to the control sample. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In yet other embodiments, the phosphorylated Tau is phosphorylated on one or more serine, threonine, or tyrosine residues. In still other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the level of phosphorylated Tau is determined by assaying the level of phosphorylated Tau polynucleotide, phosphorylated Tau polypeptide, or phosphorylated Tau activity. In yet other embodiments, the phosphorylated IRS-1 is phosphorylated on one or more serine, threonine, or tyrosine residues. In still other embodiments, the phosphorylated IRS-1 is phosphorylated at one or more residues selected from the group consisting of P-S312-IRS-1 and P-panY-IRS-1. In other embodiments, the level of phosphorylated IRS-1 is determined by assaying the level of phosphorylated IRS-1 polynucleotide, phosphorylated IRS-1 polypeptide, or phosphorylated IRS-1 activity. In other embodiments, the method further comprises isolating vesicles from the biological samples. In other embodiments, the vesicles are selected from the group consisting of exosomes, microparticles, microvesicles, nanosomes, extracellular vesicles, and ectosomes. In other embodiments, the method further comprises isolating exosomes from the biological sample. In certain embodiments, the isolated exosomes are selected from the group consisting of neuron-derived exosomes, astrocyte-derived exosomes, oliogodendrocyte-derived exosomes, and microglia-derived exosomes. In other embodiments, the level of one or more biomarkers is the protein, phosphorylated protein, mRNA, or miRNA level of the one or more biomarker.

The present invention also provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: isolating vesicles from a biological sample obtained from the subject; and determining the level of one or more biomarkers in the vesicles; wherein an elevated level of the one or more biomarkers in the sample compared to the level of the one or more biomarkers in a control sample is an indication of a neurodegenerative disorder, wherein at least one of the one or more biomarkers is selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In other embodiments, the vesicles are selected from the group consisting of exosomes, microparticles, microvesicles, nanosomes, extracellular vesicles, and ectosomes. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In yet other embodiments, the phosphorylated tau is phosphorylated on one or more serine, threonine, or tyrosine residues. In other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In yet other embodiments, the phosphorylated IRS-1 is phosphorylated on one or more serine, threonine, or tyrosine residues. In other embodiments, the phosphorylated IRS-1 is phosphorylated at one or more residues selected from the group consisting of P-S312-IRS-1 and P-panY-IRS-1. In still other embodiments, the isolated exosomes are selected from the group consisting of neuron-derived exosomes, astrocyte-derived exosomes, oliogodendrocyte-derived exosomes, and microglia-derived exosomes. In other embodiments, the isolating vesicles from a biological sample comprises: contacting the biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In other embodiments, the isolating vesicles from a biological sample comprises: isolating vesicles from said biological sample to obtain a vesicle sample; contacting the vesicle sample with an agent under conditions wherein a vesicle present in said vesicle sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In certain aspects, the agent is an antibody, a lectin, a ligand, a soluble receptor, a binding protein, or an oligonucleotide. In other aspects, the antibody is a polyclonal or monoclonal antibody. In yet other aspects, the antibody is a monoclonal NCAM antibody. In other aspects, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In other embodiments, the vesicles are selected from the group consisting of exosomes, microparticles, microvesicles, nanosomes, extracellular vesicles, and ectosomes. In other embodiments, the level of one or more biomarkers is the protein, phosphorylated protein, mRNA, or miRNA level of the one or more biomarker.

The present invention provides methods of diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, comprising: obtaining a biological sample from the subject; applying an antibody specific for vesicles to the sample, wherein the presence of the vesicle creates an antibody-vesicle complex; isolating the antibody-vesicle complex; assaying a level of one or more biomarkers in the antibody-vesicle complex; and diagnosing or prognosing a neurodegenerative disorder in a subject, identifying a subject at risk of a neurodegenerative disorder, or prescribing a therapeutic regimen or predicting benefit from therapy in a subject having a neurodegenerative disorder based on the levels of the one or more biomarkers, wherein at least one of the biomarkers are selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In some embodiments, the antibody-vesicle complex is created on a solid phase. In yet other embodiments, the methods further comprise releasing the vesicle from the antibody-vesicle complex. In certain embodiments, the solid phase is non-magnetic beads, magnetic beads, agarose, or sepharose. In other embodiments, the vesicle is released by exposing the antibody-vesicle complex to low pH between 3.5 and 1.5. In yet other embodiments, the released vesicle is neutralized by adding a high pH solution. In other embodiments, the released vesicle is lysed by incubating the released vesicles with a lysis solution. In still other embodiments, the lysis solution contains inhibitors for proteases and phosphatases. In other embodiments, the levels of the one or more biomarkers are normalized by the number of vesicles or values of vesicle biomarkers. In other embodiments, the vesicles are selected from the group consisting of exosomes, microparticles, microvesicles, nanosomes, extracellular vesicles, and ectosomes. In certain embodiments, the antibody is a polyclonal or monoclonal antibody. In other embodiments, the antibody is a monoclonal NCAM antibody. In other embodiments, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In some embodiments, the exosomes are selected from the group consisting of neuron-derived exosomes, astrocyte-derived exosomes, oliogodendrocyte-derived exosomes, and microglia-derived exosomes. In other embodiments, the phosphorylated tau is phosphorylated on one or more serine, threonine, or tyrosine residues. In still other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the phosphorylated IRS-1 is phosphorylated on one or more serine, threonine, or tyrosine residues. In still other embodiments, the phosphorylated IRS-1 is phosphorylated at one or more residues selected from the group consisting of P-S312-IRS-1 and P-panY-IRS-1. In yet other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the level of one or more biomarkers is the protein, phosphorylated protein, mRNA, or miRNA level of the one or more biomarker.

The present invention provides sets of biomarkers for assessing neurodegenerative disorder status of a subject comprising one or more biomarkers, wherein the levels of the biomarkers in the set are assayed; and wherein the biomarker level determines the neurodegenerative disorder status of the subject with at least 40% specificity, wherein the at least one or more of the set of biomarkers are selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In some embodiments, the biomarker level determines the neurodegenerative disorder status of the subject with at least 40%, 50%, 60%, 70%, 75%, 80%, 85%, 90%, 95%, 99%, or 100% specificity. the In some embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In yet other embodiments, the methods further comprise assaying the levels of the biomarkers in vesicles from the sample. In other embodiments, the vesicles are selected from the group consisting of exosomes, microparticles, microvesicles, nanosomes, extracellular vesicles, and ectosomes.

The present invention also provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds vesicles, one or more agents which specifically bind a biomarker, one or more containers for collecting and or holding the biological sample, and an instruction for its use, wherein the neurodegenerative disorder is associated with altered biomarker levels and wherein the biomarker is selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In other embodiments, the vesicles are selected from the group consisting of exosomes, microparticles, microvesicles, nanosomes, extracellular vesicles, and ectosomes. In some embodiments, the agents are polyclonal or monoclonal antibodies. In other embodiments, the antibodies are a monoclonal NCAM antibody. In other embodiments, the antibody is a monoclonal anti-human NCAM antibody. In yet other aspects, the antibody is a monoclonal CD171 antibody. In other aspects, the antibody is a monoclonal anti-human CD171 antibody. In other aspects, the antibody is a monoclonal CD9 antibody. In other aspects, the antibody is a monoclonal CD63 antibody. In other aspects, the antibody is a monoclonal CD81 antibody. In certain embodiments, the exosomes are selected from the group consisting of neuron-derived exosomes, astrocyte-derived exosomes, oliogodendrocyte-derived exosomes, and microglia-derived exosomes. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In yet other embodiments, the biological sample is selected from the group consisting of whole blood, serum, plasma, urine, interstitial fluid, peritoneal fluid, cervical swab, tears, saliva, buccal swab, skin, cerebrospinal fluid. In still other embodiments, the phosphorylated tau is phosphorylated on one or more serine, threonine, or tyrosine residues. In other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In still other embodiments, the phosphorylated IRS-1 is phosphorylated on one or more serine, threonine, or tyrosine residues. In other embodiments, the phosphorylated IRS-1 is phosphorylated at one or more residues selected from the group consisting of P-S312-IRS-1 and P-panY-IRS-1. In other embodiments, the kits further comprise a computer model or algorithm for analyzing the biomarker level in the sample.

The present invention also provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, the kit comprising one or more agents which specifically binds vesicles, one or more probes or primers for detecting biomarker mRNA or miRNA, one or more containers for collecting and or holding the biological sample, and an instruction for its use, wherein the neurodegenerative disorder is associated with altered biomarker levels and wherein the biomarker is selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In other embodiments, the vesicles are selected from the group consisting of exosomes, microparticles, microvesicles, nanosomes, extracellular vesicles, and ectosomes. In some embodiments, the agents are polyclonal or monoclonal antibodies. In other embodiments, the exosomes are selected from the group consisting of neuron-derived exosomes, astrocyte-derived exosomes, oliogodendrocyte-derived exosomes, and microglia-derived exosomes. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In still other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the phosphorylated tau is phosphorylated on one or more serine, threonine, or tyrosine residues. In still other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the phosphorylated IRS-1 is phosphorylated on one or more serine, threonine, or tyrosine residues. In still other embodiments, the phosphorylated IRS-1 is phosphorylated at one or more residues selected from the group consisting of P-S312-IRS-1 and P-panY-IRS-1. In other embodiments, the kits further comprise a computer model or algorithm for analyzing the biomarker level in the sample.

In other embodiments, the present invention provides methods of diagnosing a neurodegenerative disorder in a subject, comprising the steps of: (i) obtaining a test biological sample containing vesicles from the subject, (ii) measuring the level of one or more biomarkers in the test biological sample, (iii) comparing the level of the one or more biomarkers in the test biological sample to a control level of the one or more biomarkers in a control biological sample, and (iv) determining the subject has a neurodegenerative disorder by detecting an increased level of the one or more biomarkers in the test biological sample, relative to the control biological sample, wherein at least one of the one or more biomarkers is selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In other embodiments, the vesicles are selected from the group consisting of exosomes, microparticles, microvesicles, nanosomes, extracellular vesicles, and ectosomes. In some embodiments, the exosomes are selected from the group consisting of neuron-derived exosomes, astrocyte-derived exosomes, oliogodendrocyte-derived exosomes, and microglia-derived exosomes. In other embodiments, the phosphorylated tau is phosphorylated on one or more serine, threonine, or tyrosine residues. In still other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the phosphorylated IRS-1 is phosphorylated on one or more serine, threonine, or tyrosine residues. In still other embodiments, the phosphorylated IRS-1 is phosphorylated at one or more residues selected from the group consisting of P-S312-IRS-1 and P-panY-IRS-1. In yet other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In still other embodiments, the biological sample is selected from the group consisting of whole blood, serum, plasma, urine, interstitial fluid, peritoneal fluid, cervical swab, tears, saliva, buccal swab, skin, cerebrospinal fluid. In other embodiments, the phosphorylated tau is phosphorylated on one or more serine, threonine, or tyrosine residues. In other embodiments, the phosphorylated IRS-1 is phosphorylated on one or more serine, threonine, or tyrosine residues. In other embodiments, the method further comprises isolating vesicles from the biological sample. In other embodiments, the vesicles are selected from the group consisting of exosomes, microparticles, microvesicles, nanosomes, extracellular vesicles, and ectosomes.

In other embodiments, the present invention provides methods for analyzing a sample from a subject comprising the steps of: (i) obtaining a biological sample comprising vesicles from the subject, (ii) measuring the level of one or more biomarkers in the biological sample, and (iii) comparing the level of the one or more biomarkers in the biological sample to a control level of the one or more biomarkers in a control biological sample. In some embodiments, the subject has been diagnosed or suspected of having a neurodegenerative disorder. In other embodiments, the method further comprises diagnosing or prognosing a neurodegenerative disorder in the subject, identifying risk of a neurodegenerative disorder in the subject, or prescribing a therapeutic regimen or predicting benefit from therapy for the subject having or suspected of having a neurodegenerative disorder. In certain embodiments, at least one of the one or more biomarkers are selected from the group consisting of Tau, phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In some embodiments, the level of the one or more biomarkers in the biological sample is compared to the level of one or more biomarkers in a control sample and wherein the level of the one or more biomarkers of the biological sample is elevated compared to the control sample. In other embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease. In other embodiments, the biological sample is selected from the group consisting of whole blood, serum, plasma, urine, interstitial fluid, peritoneal fluid, cervical swab, tears, saliva, buccal swab, skin, brain tissue, and cerebrospinal fluid. In yet other embodiments, the phosphorylated Tau is phosphorylated on one or more serine, threonine, or tyrosine residues. In still other embodiments, the phosphorylated Tau is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the level of phosphorylated Tau is determined by assaying the level of phosphorylated Tau polynucleotide, phosphorylated Tau polypeptide, or phosphorylated Tau activity. In yet other embodiments, the phosphorylated IRS-1 is phosphorylated on one or more serine, threonine, or tyrosine residues. In still other embodiments, the phosphorylated IRS-1 is phosphorylated at one or more residues selected from the group consisting of P-S312-IRS-1 and P-panY-IRS-1. In other embodiments, the level of phosphorylated IRS-1 is determined by assaying the level of phosphorylated IRS-1 polynucleotide, phosphorylated IRS-1 polypeptide, or phosphorylated IRS-1 activity. In other embodiments, the method further comprises isolating vesicles from the biological samples. In other embodiments, the vesicles are selected from the group consisting of exosomes, microparticles, microvesicles, nanosomes, extracellular vesicles, and ectosomes. In other embodiments, the method further comprises isolating exosomes from the biological sample. In certain embodiments, the isolated exosomes are selected from the group consisting of neuron-derived exosomes, astrocyte-derived exosomes, oliogodendrocyte-derived exosomes, and microglia-derived exosomes. In other embodiments, the method further comprises determining a ratio of P-S312-IRS-1 and P-panY-IRS-1 (R or insulin resistance index). In other embodiments, the methods of the present invention further comprise a computer model or algorithm for analyzing the one or more biomarker level in the sample. In other embodiments, the level of one or more biomarkers is the protein, phosphorylated protein, mRNA, or miRNA level of the one or more biomarker.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items. It must be noted that as used herein and in the appended claims, the singular forms "a," "an," and "the" include plural references unless context clearly dictates otherwise.

DESCRIPTION OF THE INVENTION

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms "a," "an," and "the" include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) Remington's Pharmaceutical Sciences, 18th ed., Mack Publishing Co.; Colowick, S. et al., eds., Methods In Enzymology, Academic Press, Inc.; Handbook of Experimental Immunology, Vols. I-IV (D. M. Weir and C. C. Blackwell, eds., 1986, Blackwell Scientific Publications); Maniatis, T. et al., eds. (1989) Molecular Cloning: A Laboratory Manual, 2nd edition, Vols. I-III, Cold Spring Harbor Laboratory Press; Ausubel, F. M. et al., eds. (1999) Short Protocols in Molecular Biology, 4th edition, John Wiley & Sons; Ream et al., eds. (1998) Molecular Biology Techniques: An Intensive Laboratory Course, Academic Press); PCR (Introduction to Biotechniques Series), 2nd ed. (Newton & Graham eds., 1997, Springer Verlag).

The present invention relates, in part, to the discovery that exosomal biomarkers can be assayed to identify subjects having or likely to develop neurodegenerative disorders, including, for example, Alzheimer's disease (AD), multiple sclerosis (MS), and frontotemporal dementia (FTD).

The present invention is based, in part, on the discovery of unexpected increases in certain biomarkers in neuron-derived exosomes present in the circulation of subjects having neurodegenerative disease (e.g., Alzheimer's disease). The present invention demonstrates that exosomal levels of these biomarkers may be assayed to diagnose a neurodegenerative disorder in a subject having a neurodegenerative disease. The present invention further shows that measurement of certain biomarkers in neuron-derived exosomes from a subject may be used to predict the subsequent development of a neurodegenerative disease (e.g., identify a subject at risk of developing a neurodegenerative disorder).

The present invention provides a set of biomarkers for assessing neurodegenerative status of a subject. In this embodiment, biomarker levels are assayed and the biomarker level determines the neurodegenerative status of the subject with at least 40% specificity.

The present invention also provides compositions for use in the methods described herein. Such compositions may include small molecule compounds; peptides and proteins including antibodies or functionally active fragments thereof; and polynucleotides including small interfering ribonucleic acids (siRNAs), micro-RNAs (miRNAs), ribozymes, and anti-sense sequences. (See, e.g., Zeng (2003) Proc Natl Acad Sci USA 100:9779-9784; and Kurreck (2003) Eur J Biochem 270:1628-1644.)

The present invention further provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder. In these embodiments, the kits comprise one or more antibodies which specifically binds exosomes, one or more antibodies which specifically bind a biomarker, one or more containers for collecting and or holding the biological sample, and an instruction for the kits use.

The section headings are used herein for organizational purposes only, and are not to be construed as in any way limiting the subject matter described herein.

Biological Sample

The present invention provides biomarkers and diagnostic and prognostic methods for Alzheimer's disease and other neurodegenerative disorders. Biomarkers levels are determined in a biological sample obtained from a subject. In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter. In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues.

Enrichment or Isolation of Vesicles (Exosomes, Microparticles, Microvesicles, Nanosomes, Extracellular Vesicles, and Ectosomes)

Samples can be enriched for vesicles through positive selection, negative selection, or a combination of positive and negative selection. In some embodiments, vesicles are directly captured. In other embodiments, blood cells are captured and vesicles are collected from the remaining biological samples. In some embodiments, the vesicles enriched in the biological samples are exosomes, microparticles, microvesicles, nanosomes, extracellular vesicles, or ectosomes. In some embodiments, the vesicles enriched in the biological samples are neuron-derived exosomes, astrocyte-derived exosomes, oliogodendrocyte-derived exosomes, and microglia-derived exosomes.

Samples can also be enriched for vesicles based on differences in the biochemical properties of vesicles. For example, samples can be enriched for vesicles based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used. In some of the embodiments based on metabolic differences, dye uptake/exclusion measured by flow cytometry or another sorting technology is used. In some of the embodiments based on gene expression, cell culture with cytokines is used. Samples can also be enriched for vesicles based on other biochemical properties known in the art. For example, samples can be enriched for vesicles based on pH or motility. Further, in some embodiments, more than one method is used to enrich for vesicles. In other embodiments, samples are enriched for vesicles using antibodies, ligands, or soluble receptors.

In other embodiments, surface markers are used to positively enrich vesicles in the sample. In some embodiments, the vesicles are exosomes, microparticles, microvesicles, nanosomes, extracellular vesicles, or ectosomes. In other embodiments, NCAM, CD171, CD9, CD63, CD81, diverse neuron or astrocyte adhesive proteins, microglial CD18/11, or CD3 T cell membrane cell surface markers are used to enrich for exosomes. In some embodiments, cell surface markers that are not found on vesicles populations are used to negatively enrich vesicles by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in vesicles. Cell surface markers may include antibodies against cell surface antigens that are preferentially expressed on exosomes (e.g., NCAM). In some embodiments, the cell surface marker is a neuron-derived exosome surface marker, including, for example, NCAM or CD171. In some embodiments, a monoclonal NCAM, CD9, CD63, CD81 or CD171 antibody is used to enrich or isolate exosomes from the sample. In certain aspects, the NCAM, CD9, CD63, CD81 or CD171 antibody is biotinylated. In this embodiment, biotinylated NCAM or CD171 antibody can form an antibody-exosome complex that can be subsequently isolated using streptavidin-agarose resin or beads. In other embodiments, the NCAM, CD9, CD63, CD81 or CD171 antibody is a monoclonal anti-human NCAM, CD9, CD63, CD81 or CD171 antibody.

In some embodiments, enriched vesicles from the biological sample are subsequently enriched for a specific type of vesicle. For example, the biological sample is enriched for exosomes and then the enriched exosomes are subsequently enriched for neural-derived exosomes. In some embodiments, the biological sample is enriched for individual neural cell sources of vesicles. In certain aspects, the neural cell sources of vesicles are microglia, neurons, or astrocytes.

In other embodiments, vesicles are isolated or enriched from a biological sample comprising: contacting a biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample. In certain embodiments, the agent is an antibody or a lectin. Lectins useful for forming a vesicle-lectin complex are described in U.S. Patent Application Publication No. 2012/0077263. In some embodiments, the vesicle is an exosome, a microparticle, a microvesicle, nanosomes, extracellular vesicles, or an ectosome. In some embodiments, the exosomes are neuron-derived exosomes, astrocyte-derived exosomes, oliogodendrocyte-derived exosomes, or microglia-derived exosomes. In some embodiments, multiple isolating or enriching steps are performed. In certain aspects of the present embodiment, a first isolating step is performed to isolate exosomes from a blood sample and a second isolating step is performed to isolate neural-derived exosomes from other exosomes. In other embodiments, the vesicle portion of the vesicle-agent complex is lysed using a lysis reagent and the protein levels of the lysed vesicle are assayed. In some embodiments, the antibody-vesicle complex is created on a solid phase. In yet other embodiments, the methods further comprise releasing the vesicle from the antibody-vesicle complex. In certain embodiments, the solid phase is non-magnetic beads, magnetic beads, agarose, or sepharose. In other embodiments, the vesicle is released by exposing the antibody-vesicle complex to low pH between 3.5 and 1.5. In yet other embodiments, the released vesicle is neutralized by adding a high pH solution. In other embodiments, the released vesicle is lysed by incubating the released vesicles with a lysis solution. In still other embodiments, the lysis solution contains inhibitors for proteases and phosphatases.

Neurodegenerative Disorders

The present invention provides methods for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder.

In some embodiments the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

In some embodiments, the present invention enables a medical practitioner to diagnose or prognose one or more neurodegenerative disorder in a subject. In other embodiments, the present invention enables a medical practitioner to rule out or eliminate one or more neurodegenerative diseases as a diagnostic possibility. In yet other embodiments, the present invention enables a medical practitioner to identify a subject at risk of developing a neurodegenerative disorder. In other embodiments, the present invention enables a medical practitioner to predict whether a subject will later develop a neurodegenerative disorder. In further embodiments the present invention enables a medical practitioner to prescribe a therapeutic regimen or predict benefit from therapy in a subject having a neurodegenerative disorder.

Biomarkers

Biomarker levels are assayed in a biological sample obtained from a subject having or at-risk of having a neurodegenerative disorder (e.g., Alzheimer's disease). In some embodiments, the biomarker is phosphorylated Tau, Aβ1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171. In other embodiments, the phosphorylated tau is phosphorylated at one or more serine residues. In certain aspects of the present embodiment, the phosphorylated tau is phosphorylated on at least one serine residue selected from the group consisting of Ser-199, Ser-202, Ser-214, Ser-235, Ser-262, Ser-356, Ser-396, and Ser-422. In other embodiments, the phosphorylated tau is phosphorylated at one or more threonine residues. In certain aspects of the present embodiment, the phosphorylated tau is phosphorylated on at least one threonine residue selected from the group consisting of Thr-153, Thr-181, Thr-205, and Thr-231. In yet other embodiments, the phosphorylated tau is phosphorylated at one or more tyrosine residues. In certain aspects of the present embodiment, the phosphorylated tau is phosphorylated on at least one tyrosine residue selected from the group consisting of Tyr18, Tyr29, Tyr197, Tyr310, and Tyr 394. In other embodiments, phosphorylated tau levels are determined or assayed using antibodies against one or more phosphorylation sites. In certain aspects of the present embodiment, the antibodies used in the present invention preferentially bind to phosphorylated tau that is phosphorylated at one or more of the following phosphorylation sites: Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. In other embodiments, the phosphorylated IRS-1 is P-S312-IRS-1 or P-panY-IRS-1.

In some embodiments, biomarker levels of the present invention are measured by determining the gene expression of the biomarker. In certain embodiments, gene expression changes are measured by determining the expression level of one or more of the genes shown in Table 1. In certain aspects, gene expression of the biomarker is determined using PCR, microarray, or sequencing. In some embodiments, the expression level of the biomarker is determined by measuring the mRNA or miRNA level of the biomarker.

One of ordinary skill in the art has several methods and devices available for the detection and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings. The ratio of P-S312-IRS-1 and P-panY-IRS-1 (R or insulin resistance index) may be used to predict risk or diagnosis of a neurodegenerative disorder.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of neurodegenerative disorders (e.g., Alzheimer's disease). Markers of such disorders are typically substances found in a bodily sample that can be measured. The measured amount can correlate to underlying disorder or disease pathophysiology, presence or absence of a neurodegenerative disorder, probability of a neurodegenerative disorder in the future. In patients receiving treatment for their condition the measured amount will also correlate with responsiveness to therapy.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention may be used in clinical assays to diagnose or prognose a neurodegenerative disorder in a subject, identify a subject at risk of a neurodegenerative disorder, and/or for prescribing a therapeutic regimen or predicting benefit from therapy in a subject having a neurodegenerative disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a neurodegenerative disorder in a subject, identifying a subject at risk of a neurodegenerative disorder, or for prescribing a therapeutic regimen or predicting benefit from therapy in a subject having a neurodegenerative disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize a biomarker associated with a neurodegenerative disorder, wherein the biomarker is phosphorylated tau, Aβ1-42, phosphorylated IRS, CTSD, LAMP1, UBP, HSP70, NSE, NFL, CD9, CD63, CD81, and CD171. In some embodiments, the composition enhances the activity of at least one tau or IRS-1 phosphatase. In other embodiments, the composition decreases the activity of at least one tau or IRS-1 kinase. In yet other embodiments, the composition is selected from the group consisting of a peptide, a nucleic acid, an antibody, and a small molecule.

In certain embodiments, the present invention relates to compositions that specifically detect a biomarker associated with a neurodegenerative disorder. As detailed elsewhere herein, the present invention is based upon the finding that phosphorylated tau, phosphorylated IRS-1, CTSD, LAMP1, UBP, HSP70, NSE, and NFL are specific biomarkers for AD and other neurodegenerative disorders. In one embodiment, the compositions of the invention specifically bind to and detect phosphorylated tau. In one embodiment the compositions of the invention specifically bind to and detect tau phosphorylated at one or more serine, threonine, or tyrosine residues on tau. In some embodiments, the compositions of the invention specifically bind to tau phosphorylated at S396 (S396 tau phosphorylation). In some embodiments, the compositions of the invention specifically bind to tau phosphorylated at T181 (T181 tau phosphorylation). In still other embodiments, the compositions of the invention specifically bind to tau phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394. The composition of the present invention can comprise an antibody, a peptide, a small molecule, a nucleic acid, and the like. In other embodiments, the compositions of the present invention specifically bind to and detect phosphorylated IRS-1. In one embodiment the compositions of the invention specifically bind to and detect P-S312-IRS-1 or P-panY-IRS-1. In other embodiments, the compositions of the present invention specifically bind to and detect CTSD, LAMP1, UBP, HSP70, NSE, NFL, CD9, CD63, CD81, and CD171.

In some embodiments, the composition comprises an antibody, where the antibody specifically binds to a biomarker or vesicles of the invention. The term "antibody" as used herein and further discussed below is intended to include fragments thereof which are also specifically reactive with a biomarker or vesicle (e.g., exosome). Antibodies can be fragmented using conventional techniques and the fragments screened for utility in the same manner as described above for whole antibodies. For example, F(ab)$_2$ fragments can be generated by treating antibody with pepsin. The resulting F(ab)$_2$ fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')$_2$, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present invention, including, for example, neuron-derived exosome, phosphorylated Tau, Aβ1-42, phosphorylated IRS-1, CTSD, LAMP1, UBP, HSP70, NSE, NFL, CD9, CD63, CD81, and CD171.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a neurodegenerative disorder. As detailed elsewhere herein, the present invention is based upon the findings that tau phosphorylation is implicated in the pathology of a variety of neurodegenerative disorders, such as, for example, Alzheimer's disease. Therefore, in one embodiment, the present invention provides compositions that prevent tau phosphorylation. In one embodiment, the compositions prevent tau phosphorylation at one or more serine residues on tau. In other embodiments, the compositions prevent tau phosphorylation at one or more threonine residues on tau. In other embodiments, the compositions prevent tau phosphorylation at one or more tyrosine residues on tau. In another embodiment, the present invention provides compositions that reduce tau phosphorylation. In one embodiment, the compositions reduce tau phosphorylation at one or more serine, threonine, and/or tyrosine residues on tau. In yet other embodiments, the compositions reduce tau phosphorylation at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, and Tyr 394.

In some embodiments, the present invention relates to compositions used for treating or preventing a neurodegenerative disorder. As detailed elsewhere herein, the present invention is based upon the findings that IRS-1 phosphorylation is implicated in the pathology of a variety of neurodegenerative disorders, such as, for example, Alzheimer's disease. Therefore, in one embodiment, the present invention provides compositions that prevent IRS-1 phosphorylation. In another embodiment, the present invention provides compositions that reduce IRS-1 phosphorylation.

Compositions useful for preventing and/or reducing tau or IRS-1 phosphorylation include proteins, peptides, nucleic acids, small molecules, and the like.

Methods of Treatment

The present invention provides methods of treating a neurodegenerative disorder in a subject, comprising administering to the subject an effective amount of a composition, wherein the composition reduces the level of tau and/or IRS-1 phosphorylation. In other embodiments, the composition enhances the activity of at least one tau or IRS-1 phosphatase. In yet other embodiments, the composition reduces the activity of at least one tau or IRS-1 kinase. In other embodiments, the composition is selected from the group consisting of a peptide, a nucleic acid, an antibody, and a small molecule. In other embodiments, the present invention provides methods of treating a neurodegenerative disorder in a subject, comprising administering to the subject an effective amount of a composition, wherein the composition reduces the level of CTSD, LAMP1, or UBP. In yet other embodiments, the present invention provides methods of treating a neurodegenerative disorder in a subject, comprising administering to the subject an effective amount of a composition, wherein the composition increases the level of HSP70. In other embodiments, the present invention provides methods of treating a neurodegenerative disorder in a subject, comprising administering to the subject an effective amount of a composition, wherein the composition normalizes the level of phosphorylated tau, Aβ1-42, phosphorylated IRS-1, CTSD, LAMP1, UBP, HSP70, NSE NFL, CD9, CD63, CD81, and CD171 to a reference level.

Kits

Another aspect of the invention encompasses kits for detecting or monitoring a neurodegenerative disorder in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In further aspects, the means for enriching or isolating exosomes comprises reagents necessary to enrich or isolate exosomes from a biological sample. In certain aspects, the kit comprises a means for quantifying the amount of a biomarker. In further aspects, the means for quantifying the amount of a biomarker comprises reagents necessary to detect the amount of a biomarker.

These and other embodiments of the present invention will readily occur to those of ordinary skill in the art in view of the disclosure herein.

EXAMPLES

The invention will be further understood by reference to the following examples, which are intended to be purely exemplary of the invention. These examples are provided solely to illustrate the claimed invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description. Such modifications are intended to fall within the scope of the appended claims.

Example 1: Neuron-Derived Serum Exosomal Phosphorylated Tau and Aβ1-42 Levels in Human Subjects with Alzheimer's Disease Levels of Phosphorylated Tau and Aβ1-42 protein were assayed in human subjects with Alzheimer's disease (AD) as follows. Ten milliliters of venous blood were collected from control subjects (n=20) and subjects with AD (n=20). A first blood sample was collected at a time when AD subjects were cognitively intact. A second blood sample was collected after AD subjects had developed probable AD. The diagnosis of AD was established by standard clinical and laboratory criteria.

TABLE 1

| Gene | Entrez Gene Name | Location |
|---|---|---|
| microtubule-associated protein tau | MAPT | Chromosome 17, NC_000017.11 (45894336 . . . 46028334) |
| amyloid beta (A4) precursor protein | APP | Chromosome 21, NC_000021.9 (25880550 . . . 26171128) |
| TAR DNA-binding protein 43 | TARDBP | Chromosome 1, NC_000001.11 (11012622 . . . 11025492) |
| Alpha-synuclein | SNCA | Chromosome 4, NC_000004.12 (89724099 . . . 89838296) |
| superoxide dismutase 1 | SOD1 | Chromosome 21, NC_000021.9 (31659622 . . . 31668931) |
| FUS RNA binding protein | FUS | Chromosome 16, NC_000016.10 (31180110 . . . 31194871) |
| FK506 binding protein 51 | FKBP51 | Chromosome 6, NC_000006.12 (35573585 . . . 35728583) |
| insulin receptor substrate 1 | IRS1 | Chromosome 2, NC_000002.12 (226731317 . . . 226799829) |
| cathepsin D | CTSD | Chromosome 11, NC_000011.10 (1752752 . . . 1763992) |
| lysosomal-associated membrane protein 1 | LAMP1 | Chromosome 13, NC_000013.11 (113297154 . . . 113323426) |
| ubiquitin B | UBB | Chromosome 17, NC_000017.11 (16380793 . . . 16382745) |
| Ubiquitin C | UBC | Chromosome 12, NC_000012.12 (124911646 . . . 124915041) |
| ubiquitin A-52 residue ribosomal protein fusion product 1 | UBA52 | Chromosome 19, NC_000019.10 (18563766 . . . 18577460) |
| ribosomal protein S27a | RPS27A | Chromosome 2, NC_000002.12 (55231903 . . . 55235853) |
| heat shock 70 kDa protein 1A | HSPA1A | Chromosome 6, NC_000006.12 (31815514 . . . 31817942) |
| heat shock 70 kDa protein 4 | HSPA4 | Chromosome 5, NC_000005.10 (133051970 . . . 133105017) |
| enolase 2 (gamma, neuronal) | ENO2 | Chromosome 12, NC_000012.12 (6914450 . . . 6923696) |
| neurofilament, light polypeptide | NEFL | Chromosome 8, NC_000008.11 (24950955 . . . 24956869, complement) |

For blood collection, 10 ml of venous blood were taken from each subject and held at 37° C. for 45 min and centrifuged at 1,000×g for 20 min at 4° C. to obtain serum for storage in 0.5 ml aliquots at −80° C. Next, 0.5 ml of each serum sample was mixed with 0.5 ml of calcium- and magnesium-free Dulbecco's balanced salt solution (DBS) containing twice the recommended concentrations of protease inhibitor cocktail (Roche Applied Sciences, Inc., Indianapolis, Ind.) phosphatase inhibitor cocktail (Pierce Halt, Thermo Scientific, Inc., Rockford, Ill.), and incubated for 15 minutes at room temperature.

For plasma, 0.5 ml received 0.1 ml of thromboplastin-D (Fisher Scientific, Inc., Hanover Park, Ill.) followed by incubation at room temperature for 30 min and centrifugation at 1,500×g for 5 min. Then 0.4 ml of DBS containing 2.5-times the recommended concentrations of protease and phosphatase inhibitor cocktails were added to each supernatant.

These serum and plasma supernatants were mixed thoroughly with 252 µl of ExoQuick exosome precipitation solution (EXOQ; System Biosciences, Inc., Mountainview, Calif.), and the mixture incubated for 1 hour at 4° C. The resulting exosome suspensions were centrifuged at 1,500×g for 30 min at 4° C., the supernatants removed and each pellet of exosomes resuspended in 250 µl of DBS with the cocktails of protease and phosphatase inhibitors for immunochemical enrichment of exosomes from a neural source. Next, each sample received 2 µg of mouse anti-human NCAM antibody (ERIC 1, sc-106, Santa Cruz Biotechnology, Santa Cruz, Calif.), that had been previously biotinylated with the EZ-Link sulfo-NHS-biotin system (Thermo Scientific, Inc.). After 2 hr at 4° C., 20 µl of streptavidin-agarose resin (Thermo Scientific, Inc.) was added to each sample followed by incubation for 1 hr at 4° C. with rocking. The samples then were centrifuged at 200 g for 10 min at 4° C., the supernates removed and each pellet resuspended in 250 µl of ELISA binding buffer (System Biosciences, Inc.) with the cocktails of protease and phosphatase inhibitors.

Neuron-derived exosomal proteins were quantified by ELISA kits for human CD81 (System Biosciences, Inc. and Hölzel Diagnostika, Cologne, Germany) with verification of antigen with human purified recombinant CD81 antigen (Origene Technologies, Inc., Rockville, Md.), human Aβ1-42, total human tau and human phosphorylated tau [pS396] (Life Technologies/Invitrogen, Camarillo, Calif.), and human phosphorylated tau [pT181] (Innogenetics, Inc., Alpharetta, Ga.) according to the suppliers' directions.

As shown in Table 2 below, neuron-derived serum exosomal phosphorylated Tau (pS396) levels were significantly increased in subjects with AD compared to control subject serum exosomal levels. Similarly, serum exosomal Aβ1-42 levels were significantly increased in subjects with AD compared to control levels. Serum exosomal total Tau levels were not significantly different between AD and control subjects.

TABLE 2

| Group | Total Tau (pg/ml) | Aβ1-42 (pg/ml) | pS396 Tau (pg/ml) |
|---|---|---|---|
| AD (n = 20) | 290 ± 160 | 14.28 ± 4.61+ | 13.46 ± 10.38* |
| Control (n = 20) | 298 ± 125 | 9.61 ± 2.92 | 1.46 ± 0.35 |

Mean ± SD;
*p < 0.0001 compared to Control,
+p = 0.0005 by a two-tailed unpaired t test.

These results showed that neuron-derived serum exosomal levels of Aβ1-42 and phosphorylated Tau are useful for identifying subjects with AD. These results further indicated that methods and compositions of the present invention are useful for diagnosing Alzheimer's disease and other neurodegenerative disorders.

A second series of experiments were carried out to determine the levels of phosphorylated Tau and Aβ1-42 protein in human subjects with early Alzheimer's disease (i.e., minimal cognitive impairment, MCI) and late Alzheimer's disease. Ten milliliters of venous blood were collected from subjects with early AD (n=10) and subjects with late AD (n=8). Blood samples were processed as described above and neuron-derived exosomal protein levels for Aβ1-42, Tau, and phosphorylated Tau were quantified using the ELISA kits described above.

As shown in Table 3 below, neuron-derived serum exosomal phosphorylated Tau (pS396) levels were similar in early AD and late AD. Serum exosomal Aβ1-42 levels were also similar in early AD and late AD.

TABLE 3

| Group | Total Tau (pg/ml) | Aβ1-42 (pg/ml) | pS396 Tau (pg/ml) |
|---|---|---|---|
| Early AD (n = 10) | 315 ± 152 | 13.76 ± 4.27 | 13.81 ± 9.30 |
| Late AD (n = 8) | 305 ± 96 | 13.44 ± 3.11 | 13.83 ± 13.30 |

Values are mean ± SD

These results showed that neuron-derived serum exosomal levels of Aβ1-42 and phosphorylated Tau are useful for identifying subjects with early AD or late AD. These results further indicated that methods and compositions of the present invention are useful for diagnosing Alzheimer's disease and other neurodegenerative disorders.

Example 2: Neuron-Derived Serum Exosomal Phosphorylated Tau Levels in Human Subjects with Alzheimer's Disease Neuron-derived exosomal levels of phosphorylated Tau protein are assayed in human subjects with Alzheimer's disease (AD) as follows. Blood samples are collected from human subjects with AD and processed as described in Example 1 above except that, following neuron-derived exosome enrichment, the samples are assayed for the following phosphorylated Tau proteins: pSer-199 Tau, pSer-202 Tau, pSer-214 Tau, pSer-235 Tau, pSer-262 Tau, pSer-356 Tau, pSer-422 Tau, pThr-153 Tau, pThr-181 Tau, pThr-205 Tau, or pThr-231 Tau.

Neuron-derived exosomal phosphorylated Tau levels are significantly increased compared to control levels. These results show that neuron-derived serum exosomal levels of phosphorylated Tau are useful for identifying subjects with AD. These results further indicate that methods and compositions of the present invention are useful for diagnosing Alzheimer's disease and other neurodegenerative disorders.

Example 3: Neuron-Derived Serum Exosomal Protein Levels in Human Subjects with Multiple Sclerosis Levels of Phosphorylated Tau protein are assayed in human subjects with Multiple Sclerosis (MS) as follows. Blood samples are collected from human subjects with MS and processed as described in Example 1 above except that, following neuron-derived exosome enrichment, the samples are assayed for the following exosomal proteins: pSer-199 Tau, pSer-202 Tau, pSer-214 Tau, pSer-235 Tau, pSer-262 Tau, pSer-356 Tau, pSer-396 Tau, pSer-422 Tau, pThr-153 Tau, pThr-181 Tau, pThr-205 Tau, or pThr-231 Tau.

Neuron-derived exosomal phosphorylated Tau levels are significantly increased compared to control levels. These results show that neuron-derived serum exosomal levels of phosphorylated Tau are useful for identifying subjects with MS. These results further indicate that methods and compositions of the present invention are useful for diagnosing multiple sclerosis and other neurodegenerative disorders.

Example 4: Neuron-Derived Serum Exosomal Protein Levels in Human Subjects with Frontotemporal Dementia Levels of Phosphorylated Tau protein are assayed in human subjects with frontotemporal dementia (FTD) as follows. Blood samples are collected from human subjects with FTD and processed as described in Example 1 above except that, following neuron-derived exosome enrichment, the samples are assayed for the following exosomal proteins: pSer-199 Tau, pSer-202 Tau, pSer-214 Tau, pSer-235 Tau, pSer-262 Tau, pSer-356 Tau, pSer-396 Tau, pSer-422 Tau, pThr-153 Tau, pThr-181 Tau, pThr-205 Tau, or pThr-231 Tau.

Neuron-derived exosomal phosphorylated Tau levels are significantly increased compared to control levels. These results show that neuron-derived serum exosomal levels of phosphorylated Tau are useful for identifying subjects with FTD. These results further indicate that methods and compositions of the present invention are useful for diagnosing frontotemporal dementia and other neurodegenerative disorders.

Example 5: Neuron-Derived Serum Exosomal Protein Levels Predict Alzheimer's Disease in Human Subjects Neuron-derived exosomal levels of phosphorylated Tau protein are assayed in human subjects to predict Alzheimer's disease (AD) as follows (e.g., identify subjects at-risk of developing Alzheimer's disease). Blood samples are collected from human subjects prior to diagnosis of AD (e.g., prior to AD onset) and again after a diagnosis of Alzheimer's disease (e.g., after developing overt dementia). Blood samples are processed as described in Example 1 above except that, following neuron-derived exosome enrichment, the samples are assayed for the following exosomal proteins: pSer-199 Tau, pSer-202 Tau, pSer-214 Tau, pSer-235 Tau, pSer-262 Tau, pSer-356 Tau, pSer-396 Tau, pSer-422 Tau, pThr-153 Tau, pThr-181 Tau, pThr-205 Tau, or pThr-231 Tau.

Neuron-derived exosomal phosphorylated Tau levels are significantly increased compared to control levels in blood samples taken before and after AD diagnosis (i.e., increased neuron-derived exosomal phosphorylated Tau levels before AD onset and after developing overt dementia). These results show that neuron-derived serum exosomal levels of phosphorylated Tau are useful for predicting whether a subject will develop AD. These results further indicate that methods and compositions of the present invention are useful for prognosing and diagnosing Alzheimer's disease and other neurodegenerative disorders.

Example 6: Neuron-Derived Serum Exosomal Phosphorylated Tau, Total Tau, and Aβ1-42 Levels are Increased in Human Subjects with Alzheimer's Disease Exosomal levels of total Tau, phosphorylated Tau (P-T181 and P-S396), and Aβ1-42 protein levels were assayed in human subjects with Alzheimer's disease (AD) as follows. Ten milliliters of venous blood were collected from subjects with AD (n=57) and control subjects (n=57). Blood samples were processed and exosomes were isolated as described in Example 1 above.

Exosome proteins were quantified by ELISA kits for human Aβ1-42, human total tau and human P-S396-tau (Life Technologies/Invitrogen, Camarillo, Calif.), human P-T181-tau (Innogenetics Division of Fujirebio US, Inc., Alpharetta, Ga.) and human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions.

Separate discriminant classifier analyses were conducted to define the best simple linear models for comparing AD subjects with control subjects. Two discriminant analyses considered all variables and were performed step-wise. Final models retained only variables with a minimum partial F of 3.84 to enter and 2.71 to remove. Prior probabilities were considered equal for all groups. Fisher Function Coefficients and within group covariances were computed. Receiver operating characteristics (ROC) analyses were conducted under the non-parametric distribution assumption for Standard Error of Area to determine the performance of the models for discriminating AD subjects from control subjects. Discriminant and ROC analyses were conducted with SPSS v21.0 (IBM).

As shown in Table 4 below, neuron-derived serum exosomal total tau, P-T181-tau, P-S396-tau, and Aβ1-42 levels were significantly increased in subjects with AD compared to control subject serum exosomal levels.

TABLE 4

| Group | Total Tau (pg/ml) | pT181 Tau (pg/ml) | pS396 Tau (pg/ml) | Aβ1-42 (pg/ml) |
| --- | --- | --- | --- | --- |
| AD (n = 57) | 191 ± 12.3[+] | 106 ± 6.10* | 25.4 ± 2.25* | 18.5 ± 2.97* |
| Control (n = 57) | 130 ± 11.9 | 16.9 ± 1.89 | 3.88 ± 0.26 | 0.83 ± 0.13 |

Mean ± SD;
*p < 0.0001 compared to Control,
[+]p = 0.0005 by an unpaired t test.

Step-wise discriminant analyses resulted in a model progressively incorporating P-T181-tau, P-S396-tau and Aβ1-42, but not total tau, which produced a Wilk's Lambda of 0.229 and an exact F of 119 (p<0.001). The final model correctly classified 96.4% of AD patients. The Area Under the Curve (AUC) for the final model from the ROC analysis was 0.999 and individual AUC values for the individual proteins were 0.991, 0.988, 0.987 and 0.731, respectively, for P-T181-tau, P-S396-tau, Aβ1-42 and total tau.

These results showed that neuron-derived serum exosomal levels of total Tau, P-T181-tau, P-S396-tau, and Aβ1-42 are increased in subjects with Alzheimer's disease and are useful for identifying subjects with Alzheimer's disease. These results further showed that assays and methods of the present invention correctly classified subjects with Alzheimer's disease. These results further indicated that methods and compositions of the present invention are useful for diagnosing Alzheimer's disease and other neurodegenerative disorders.

Example 7: Neuron-Derived Serum Exosomal Phosphorylated Tau, Total Tau, and Aβ1-42 Levels are Increased in Human Subjects with Frontotemporal Disease Exosomal levels of total Tau, phosphorylated Tau (P-T181 and P-S396), and Aβ1-42 protein levels were assayed in human subjects with frontotemporal disease (FTD) as follows. Ten milliliters of venous blood were collected from subjects with FTD (n=16) and control subjects (n=16). Blood samples were processed and exosomes were isolated as described in Example 1 above.

Exosome proteins were quantified by ELISA kits for human Aβ1-42, human total tau and human P-S396-tau (Life Technologies/Invitrogen, Camarillo, Calif.), human P-T181-tau (Innogenetics Division of Fujirebio US, Inc., Alpharetta, Ga.) and human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions.

Separate discriminant classifier analyses were conducted to define the best simple linear models for comparing FTD subjects with control subjects. Two discriminant analyses considered all variables and were performed step-wise. Final models retained only variables with a minimum partial F of 3.84 to enter and 2.71 to remove. Prior probabilities were considered equal for all groups. Fisher Function Coefficients and within group covariances were computed. Receiver operating characteristics (ROC) analyses were conducted under the non-parametric distribution assumption for Standard Error of Area to determine the performance of the models for discriminating FTD subjects from control subjects. Discriminant and ROC analyses were conducted with SPSS v21.0 (IBM).

As shown in Table 5 below, neuron-derived serum exosomal P-T181-tau and Aβ1-42 levels were significantly increased in subjects with FTD compared to control subject serum exosomal levels.

In a step-wise discriminant analysis, P-T181-tau attained a Wilk's Lambda value of 0.324 and an exact F of 62.5 ($p<0.001$). In a final model, exosomal P-T181-tau correctly classified 87.5% of FTD patients contrasted with control subjects (75% of FTD and 100% of control). For the final model from the ROC analysis, AUC for P-T181-tau was 0.992 and for Aβ1-42 was 0.969.

These results showed that neuron-derived serum exosomal levels of P-T181-tau and Aβ1-42 are increased in subjects with frontotemporal disease and are useful for identifying subjects with frontotemporal disease. These results further showed that assays and methods of the present invention correctly classified subjects with frontotemporal disease. These results further indicated that methods and compositions of the present invention are useful for diagnosing frontotemporal disease and other neurodegenerative disorders.

Example 8: Neuron-Derived Serum Exosomal Phosphorylated Tau and AD1-42 Levels Predict Development of Alzheimer's Disease in Human Subjects Exosomal levels of total Tau, phosphorylated Tau (P-T181 and P-S396), and Aβ1-42 protein levels were assayed in human subjects as follows. Ten milliliters of venous blood were collected from subjects (n=24) at two time-points: the first at one to ten years before the subjects' diagnosis of Alzheimer's disease (Alzheimer's preclinical, AP) and the second at the time of initial diagnosis of Alzheimer's disease (AD). Venous blood samples were also collected from control subjects (n=24). Blood samples were processed and exosomes were isolated as described in Example 1 above.

Exosome proteins were quantified by ELISA kits for human Aβ1-42, human total tau and human P-S396-tau (Life Technologies/Invitrogen, Camarillo, Calif.), human P-T181-tau (Innogenetics Division of Fujirebio US, Inc., Alpharetta, Ga.) and human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions.

As shown in Table 6 below, neuron-derived serum exosomal P-T181-tau, P-S396-tau, and Aβ1-42 levels were significantly increased in subjects with AD compared to control subject serum exosomal levels. Further, neuron-derived serum exosomal P-T181-tau and P-S396-tau levels were significantly increased in subjects as early as 10 years before clinical diagnosis of AD (see Table 6). For Aβ1-42, mean levels for the AD and AP groups both were significantly higher than control subject levels, and the mean AD level also was significantly higher than that of the AP group (see Table 6).

TABLE 5

| Group | Total Tau (pg/ml) | pT181 Tau (pg/ml) | pS396 Tau (pg/ml) | Aβ1-42 (pg/ml) |
|---|---|---|---|---|
| FTD (n = 16) | 135 ± 15.8 | 82.6 ± 9.20* | 2.13 ± 0.33 | 7.54 ± 1.01* |
| Control (n = 16) | 148 ± 30.1 | 9.32 ± 2.86 | 3.13 ± 0.46 | 0.76 ± 0.35 |

Mean ± SD;
*$p < 0.0001$ compared to Control by an unpaired t test.

TABLE 6

| Group | Total Tau (pg/ml) | pT181 Tau (pg/ml) | pS396 Tau (pg/ml) | Aβ1-42 (pg/ml) |
|---|---|---|---|---|
| AD (n = 24) | 165 ± 15.8 | 91.1 ± 4.42* | 25.2 ± 1.85* | 14.5 ± 1.41* |
| AP (n = 24) | 154 ± 13.6 | 85.7 ± 3.75* | 19.2 ± 2.00* | 6.64 ± 0.58*# |
| Control (n = 16) | 148 ± 116.5 | 35.6 ± 3.49 | 4.72 ± 0.64 | 1.51 ± 0.52 |

Mean ± SEM;
*$p < 0.0001$ compared to Control by paired t test;
$p < 0.0001$ compared to AD by paired t test.

These results showed that neuron-derived serum exosomal levels of P-T181-tau, P-S396-tau, and Aβ1-42 are increased in subjects with Alzheimer's disease and are useful for identifying subjects with Alzheimer's disease. These results also showed that neuron-derived serum exosomal levels of P-T181-tau, P-S396-tau, and Aβ1-42 are increased in subjects as early as 10 years before clinical diagnosis of Alzheimer's disease. These results further showed that assays and methods of the present invention are useful for identifying a subject at risk of a neurodegenerative disorder (e.g., Alzheimer's disease). Additionally, these results showed that the assays and methods of the present invention may be useful for early detection and determining the progression of Alzheimer's disease. These results further indicated that methods and compositions of the present invention are useful for diagnosing Alzheimer's disease and other neurodegenerative disorders.

Example 9: Neuron-Derived Plasma Exosomal Total IRS-1 and Phosphorylated IRS-1 Levels in Human Subjects with a Neurodegenerative Disorder or Diabetes Exosomal levels of total IRS-1 and phosphorylated IRS-1 (P-S312-IRS-1 and P-panY-IRS-1) protein levels were assayed in human subjects as follows. Thirty milliliters of venous blood were collected from 26 subjects with AD, 20 subjects with type 2 diabetes mellitus (DM2), 16 subjects with FTD, and matched control subjects. Blood samples were incubated for 10 min at room temperature and centrifuged for 15 min at 1500 g. Plasma was aspirated and stored in aliquots at −80° C.

One-half ml of plasma was incubated with 0.15 ml of thromboplastin-D (Fisher Scientific, Inc., Hanover Park, Ill.) at room temperature for 1 hour, followed by addition of 0.35 ml of calcium- and magnesium-free Dulbecco's balanced salt solution (DBS$^{-2}$) with three-times the suggested final concentrations of protease inhibitor cocktail (Roche Applied Sciences, Inc., Indianapolis, Ind.) and phosphatase inhibitor cocktail (Pierce Halt, Thermo Scientific, Inc., Rockford, Ill.). After centrifugation at 1,500 g for 20 min, supernates were mixed with 252 µl of ExoQuick exosome precipitation solution (EXOQ; System Biosciences, Inc., Mountainview, Calif.), and incubated for 1 hour at 4° C. Resultant exosome suspensions were centrifuged at 1,500 g for 30 min at 4° C. and each pellet was re-suspended in 250 µl of distilled water with inhibitor cocktails by vortex-mixing after a −80° C. freeze-thaw cycle before immunochemical enrichment of exosomes from neural sources.

Each sample was incubated for 1 hour at 4° C. with 1 µg of mouse anti-human CD171 (L1CAM neural adhesion protein) biotinylated antibody (clone 5G3, eBioscience, San Diego, Calif.) in 50 µL of 3% BSA (1:3.33 dilution of Blocker BSA 10% solution in PBS, Thermo Scientific, Inc.) with 50 µL of 3% BSA and incubation for 30 min at 4° C. After centrifugation at 200 g for 10 min at 4° C. and removal of the supernate, each pellet was resuspended in 0.5 ml of M-PER mammalian protein extraction reagent (Thermo Scientific, Inc.), that had been adjusted to pH 8.0 with 1 M Tris-HCl (pH 8.6) and contained the cocktails of protease and phosphatase inhibitors. These suspensions were incubated at 37° C. for 20 min and vortex-mixed for 15 sec before storage at −80° C. until use in ELISAs.

Exosome proteins were quantified by ELISA kits for human P-S312-IRS-1 (Life Technologies Corp., Carlsbad, Calif.), human P-panY-IRS-1 (Cell Signaling Technology, Danvers, Mass.), human total IRS-1 (AMSBIO, LLC, Cambridge, Mass.), and tetraspanning exosome marker human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions. The mean value for all determinations of CD81 in each assay group was set at 1.00 and the relative values for each sample used to normalize their recovery. R, the insulin resistance index, was defined as the ratio of P-S312-IRS-1 and P-panY-IRS-1.

The statistical significance of differences between group means for patients with AD or FTD or DM2, and between each patient group and their respective matched control groups was determined with an unpaired t test including a Bonferroni correction in the interpretation (GraphPad Prism 6, La Jolla, Calif.). Separate discriminant classifier analyses were conducted to define the best simple linear models for comparing group AD with its control group (AC), FTD with its control group (FTC) and DM2 with its control group (DC). The discriminant analyses were performed step-wise with the Wilks' Lambda method. In each step, only variables with a minimum partial F of 3.84 to enter and 2.71 to remove were retained. Prior probabilities were considered equal for all groups. Fisher Function Coefficients and within group covariances also were computed. Receiver operating characteristics (ROC) analyses were conducted under the non-parametric distribution assumption for Standard Error of Area to determine the performance of the models for discriminating AD from AC, FTD from FTC, DM2 from DC, and AD from DM2 and FTD. Discriminant and ROC analyses were conducted with SPSS v21.0 (IBM). To assess significance of associations between CSF biomarkers in AD patients and IRS-1 proteins in neurally-enriched exosomes, we computed zero-order Pearson's correlations and partial correlations (controlling for age and sex). For longitudinal analyses, the significance of differences between serial values for AD patients taken before and after onset of aMCI or dementia was calculated with a paired t test (GraphPad).

As shown in Table 7 below, neuron-derived serum exosomal P-S312-IRS-1 levels were significantly increased in subjects with AD, DM2, and FTD compared to their respective control subject serum exosomal levels. The ratio of insulin resistance index (R) was significantly increased in subjects with AD, DM2, and FTD compared to their respective controls (see Table 7). For P-panY-IRS-1, mean levels for the AD and DM2 groups both were significantly higher than control subject levels (see Table 7).

TABLE 7

| Group | IRS-1 (pg/ml) | P-S312-IRS-1 (U/ml) | P-panY-IRS-1 (AU) | Insulin Resistance Index (R) |
|---|---|---|---|---|
| AD (n = 26) | 5.04 ± 0.10 | 7.72 ± 0.45* | 0.085 ± 0.003* | 92.2 ± 5.34* |
| AC (n = 26) | 5.45 ± 0.11 | 3.94 ± 0.30 | 0.204 ± 0.005 | 19.4 ± 1.44 |
| DM2 (n = 20) | 5.59 ± 0.12 | 5.48 ± 0.11* | 0.143 ± 0.015* | 50.4 ± 6.93* |
| DC (n = 20) | 5.34 ± 0.12 | 3.24 ± 0.14 | 0.199 ± 0.005 | 16.4 ± 0.67 |
| FTD (n = 16) | 5.54 ± 0.15 | 6.12 ± 0.37* | 0.226 ± 0.087 | 29.5 ± 2.08* |
| FTC (n = 16) | 5.30 ± 0.14 | 4.19 ± 0.18 | 0.215 ± 0.010 | 19.9 ± 1.30 |

Mean ± SEM;
*$p < 0.0001$ compared to Control by paired t test.

Step-wise discriminant analysis of AD and AC data resulted in a model that incorporated first P-panY-IRS-1 and second P-S312-IRS-1. The final model achieved a Wilks' Lambda of 0.105 and an exact F of 207.9 ($P<0.001$), and correctly classified 100% of AD patients and AC subjects. In the ROC analysis of classification of the AD and AC groups, individual subject scores from the final model achieved an area under the curve (AUC) of 1 (asymptotic significance <0.001). The AUC values were 0.722, 0.862 and 0.999, respectively, for total IRS-1, P-S312-IRS-1, and P-panY-IRS-1. Step-wise discriminant analysis of data that distinguished DM2 from DC resulted in a model that incorporated first P-panY-IRS-1 and second P-S312-IRS-1. The final model achieved a Wilks' Lambda of 0.168 and an exact F of 91.8 ($P<0.001$) and correctly classified 97.5% of DM2 patients and DC subjects. In ROC analysis of classification of the DM2 and DC groups, individual subject scores from the final model achieved an AUC of 1. The AUC values were 0.741 (asymptotic significance=0.009) and 0.999 (asymptotic significance <0.001), respectively, for P-panY-IRS-1 and P-S312-IRS-1. Step-wise discriminant analysis of data that distinguished FTD from FTC resulted in a model that incorporated P-S312-IRS-1. The final model achieved a Wilks' Lambda of 0.576 and an exact F of 22.1 ($P<0.001$) and correctly classified 84% of FTD patients and FTC subjects. In ROC analysis of classification of the FTD and FTC groups, P-S312-IRS-1 achieved an AUC of 0.928 (asymptotic significance <0.001).

These results showed that neuron-derived serum exosomal levels of P-S312-IRS-1, P-panY-IRS-1, and the ratio of insulin resistance index (R) are increased in subjects with AD, DM2, and FTD and are useful for identifying subjects with AD, DM2, and FTD. These results further indicated that methods and compositions of the present invention are useful for diagnosing Alzheimer's disease, diabetes, frontotemporal dementia and other neurodegenerative disorders.

Example 10: Neuron-Derived Serum Exosomal Phosphorylated IRS-1 Levels and an Insulin Resistance Index Predict Development of Alzheimer's Disease in Human Subjects Exosomal levels of total IRS-1 and phosphorylated IRS-1 (P-S312-IRS-1 and P-panY-IRS-1) protein levels were assayed in human subjects as follows. Ten milliliters of venous blood were collected from subjects (n=22) at two time-points: the first at one to ten years before the subjects' diagnosis of Alzheimer's disease (Alzheimer's preclinical, AP) and the second at the time of initial diagnosis of Alzheimer's disease (AD). Venous blood samples were also collected from control subjects (n=22). Blood samples were processed and exosomes were isolated as described in Example 9 above.

As shown in Table 8 below, neuron-derived serum exosomal serum exosomal P-S312-IRS-1, P-panY-IRS-1 and R were significantly increased in subjects with AD compared to control subject serum exosomal levels. Further, neuron-derived serum exosomal P-S312-IRS-1, P-panY-IRS-1 and R were significantly increased in subjects as early as 10 years before clinical diagnosis of AD (see Table 8).

TABLE 8

| Group | IRS-1 (pg/ml) | P-S312-IRS-1 (U/ml) | P-panY-IRS-1 (AU) | Insulin Resistance Index (R) |
|---|---|---|---|---|
| AP (n = 22) | 5.62 ± 130.5 | 9.22 ± 1.07* | 0.119 ± 0.016* | 92.0 ± 1.07* |
| AD (n = 22) | N/A | 9.70 ± 0.95* | 0.113 ± 0.011* | 101 ± 19.8* |
| Control (n = 22) | N/A | 2.93 ± 0.13 | 0.205 ± 0.006 | 14.7 ± 0.89 |

Mean ± SEM;
*$p < 0.0001$ compared to Control by paired t test.

These results showed that neuron-derived serum exosomal levels of P-S312-IRS-1, P-panY-IRS-1 and R are increased in subjects with Alzheimer's disease and are useful for identifying subjects with Alzheimer's disease. These results also showed that neuron-derived serum exosomal levels of P-S312-IRS-1, P-panY-IRS-1 and R are increased in subjects as early as 10 years before clinical diagnosis of Alzheimer's disease. These results further showed that assays and methods of the present invention are useful for identifying a subject at risk of a neurodegenerative disorder (e.g., Alzheimer's disease). Additionally, these results showed that the assays and methods of the present invention may be useful for early detection and determining the progression of Alzheimer's disease. These results further indicated that methods and compositions of the present invention are useful for diagnosing Alzheimer's disease and other neurodegenerative disorders.

Example 11: Neuron-Derived Plasma Exosomal Protein Levels in Human Subjects with a Neurodegenerative Disorder Exosomal levels of cathepsin D (CTSD), type 1 lysosome-associated membrane protein (LAMP1), ubiquitinylated proteins (UBP) and heat-shock protein 70 (HSP70) levels were assayed in human subjects as follows. Thirty milliliters of venous blood were collected from 26 subjects with Alzheimer's disease (AD), 16 subjects with frontotemporal dementia (FTD), and matched control subjects (Alzheimer's Controls—AC and Frontotemporal Dementia Controls—FTC). Blood samples were incubated for 10 min at room temperature and centrifuged for 15 min at 1500 g. Plasma was aspirated and stored in aliquots at −80° C.

One-half ml of plasma was incubated with 0.15 ml of thromboplastin-D (Fisher Scientific, Inc., Hanover Park, Ill.) at room temperature for 1 hour, followed by addition of 0.35 ml of calcium- and magnesium-free Dulbecco's balanced salt solution ($DBS^{-2}$) with three-times the suggested final concentrations of protease inhibitor cocktail (Roche Applied Sciences, Inc., Indianapolis, Ind.) and phosphatase inhibitor cocktail (Pierce Halt, Thermo Scientific, Inc., Rockford, Ill.). After centrifugation at 1,500 g for 20 min, supernates were mixed with 252 µl of ExoQuick exosome precipitation solution (EXOQ; System Biosciences, Inc., Mountainview, Calif.), and incubated for 1 hour at 4° C. Resultant exosome suspensions were centrifuged at 1,500 g for 30 min at 4° C. and each pellet was re-suspended in 250 µl of distilled water with inhibitor cocktails by vortex-mixing after a −80° C. freeze-thaw cycle before immunochemical enrichment of exosomes from neural sources.

Each sample was incubated for 1 hour at 4° C. with 1 µg of mouse anti-human CD171 (L1CAM neural adhesion protein) biotinylated antibody (clone 5G3, eBioscience, San Diego, Calif.) in 50 µL of 3% BSA (1:3.33 dilution of Blocker BSA 10% solution in PBS, Thermo Scientific, Inc.) with 50 µL of 3% BSA and incubation for 30 min at 4° C. After centrifugation at 200 g for 10 min at 4° C. and removal of the supernate, each pellet was resuspended in 0.5 ml of M-PER mammalian protein extraction reagent (Thermo Scientific, Inc.), that had been adjusted to pH 8.0 with 1 M Tris-HCl (pH 8.6) and contained the cocktails of protease and phosphatase inhibitors. These suspensions were incubated at 37° C. for 20 min and vortex-mixed for 15 sec before storage at −80° C. until use in ELISAs.

Exosome proteins were quantified by ELISA kits for total ubiquitin (FIVEphoton Biochemicals, San Diego, Calif.), type 1 lysosome-associated membrane protein (LAMP1) (USBiological Life Sciences, Salem, Mass.), heat-shock protein 70 (HSP70) (Enzo Life Sciences, Farmingdale, N.Y.), cathepsin D (EMD Milipore Corp., Billerica, Mass.) and tetraspanning exosome marker human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions. The mean value for all determinations of CD81 in each assay group was set at 1.00 and the relative values for each sample used to normalize their recovery.

The statistical significance of differences between group means for cross-sectional patient groups and between each patient group and their respective matched control groups was determined with an unpaired t test including a Bonferroni correction in the interpretation (GraphPad Prism 6, La Jolla, Calif.). Separate discriminant classifier analyses were conducted to define the best simple linear models for comparing group AD with its control group (AC) and FTD with its control group (FTC). The discriminant analyses were performed step-wise with the Wilks' Lambda method. In each step, only variables with a minimum partial F of 3.84 to enter and 2.71 to remove were retained. Prior probabilities were considered equal for all groups. Fisher Function Coefficients and within group covariances also were computed. Receiver operating characteristics (ROC) analyses were conducted under the non-parametric distribution assumption for Standard Error of Area to determine the performance of classifier models. For longitudinal analyses, the significance of differences between serial values for AD patients taken before and after onset of aMCI or dementia was calculated with a paired t test (GraphPad).

As shown in Table 9 below, neuron-derived serum exosomal CTSD, LAMP1, and UBP protein levels were significantly increased and HSP70 protein levels were significantly decreased in subjects with AD compared to their respective control subject serum exosomal levels. Neuron-derived serum exosomal CTSD protein levels were significantly increased and HSP70 protein levels were significantly decreased in subjects with FTD compared to their respective control subject serum exosomal levels (see Table 9).

TABLE 9

| Group | CTSD (ng/ml) | LAMP1 (pg/ml) | UBP (pg/ml) | HSP70 (pg/ml) |
|---|---|---|---|---|
| AD (n = 26) | 17.7 ± 0.80* | 1,808 ± 204* | 477 ± 25.4* | 246 ± 18.0* |
| AC (n = 26) | 8.35 ± 0.27 | 946 ± 119 | 225 ± 10.1 | 394 ± 15.2 |
| FTD (n = 16) | 12.8 ± 0.75* | 1,071 ± 62.7 | 255 ± 11.5 | 165 ± 4.39* |
| FTC (n = 16) | 6.23 ± 0.15 | 1,147 ± 88.9 | 228 ± 8.53 | 429 ± 15.6 |

Mean ± SEM;
*$p < 0.0005$ compared to Control by paired t test.

Step-wise discriminant analysis of AD and AC data resulted in a model that incorporated CTSD, then UBP and finally HSP-70, but not LAMP-1. ROC curves of AD vs. AC showed an area under the curve (AUC) of 1.0 for both CTSD and composite scores from the final model with correct classification of 100% of AD patients. Similar ROC analyses correctly classified 100% of FTD vs. FTC controls and 95.8% of AD vs. FTD.

These results showed that neuron-derived serum exosomal levels of CTSD, LAMP1, and UBP protein levels are increased and HSP70 protein levels are decreased in subjects with AD and are useful for identifying subjects with AD. These results also demonstrated that neuron-derived serum exosomal levels of CTSD are increased and HSP70 protein levels are decreased in subjects with FTD and are useful for identifying subjects with FTD. These results further indicated that methods and compositions of the present invention are useful for diagnosing Alzheimer's disease, frontotemporal dementia, and other neurodegenerative disorders.

Example 12: Neuron-Derived Serum Exosomal Protein Levels Predict Development of Alzheimer's Disease in Human Subjects Exosomal levels of cathepsin D (CTSD), type 1 lysosome-associated membrane protein (LAMP1), ubiquitinylated proteins (UBP) and heat-shock protein 70 (HSP70) levels were assayed in human subjects as follows. Ten milliliters of venous blood were collected from subjects (n=20) at two time-points: the first at one to ten years before the subjects' diagnosis of Alzheimer's disease (Alzheimer's preclinical, AP) and the second at the time of initial diagnosis of Alzheimer's disease (AD). Venous blood samples were also collected from control subjects (n=20). Blood samples were processed and exosomes were isolated as described in Example 11 above.

As shown in Table 10 below, neuron-derived serum exosomal serum exosomal CTSD, LAMP-1, and UBP were significantly increased and HSP70 protein levels were significantly decreased in subjects with AD compared to control subject serum exosomal levels. Further, neuron-derived serum exosomal CTSD, LAMP-1, and UBP were increased and HSP70 protein levels were decreased in subjects as early as 10 years before clinical diagnosis of AD (see Table 10).

TABLE 10

| Group | CTSD (ng/ml) | LAMP1 (pg/ml) | UBP (pg/ml) | HSP70 (pg/ml) |
|---|---|---|---|---|
| AP | 18.4 ± 0.68* | 2,638 ± 354* | 364 ± 13.9* | 244 ± 16.4* |
| AD | 19.0 ± 0.70* | 2,080 ± 257* | 347 ± 13.9* | 250 ± 11.8* |
| Control | 8.50 ± 0.36 | 1,035 ± 119 | 206 ± 7.46 | 392 ± 14.2 |

Mean ± SEM;
*$p < 0.0003$ compared to Control by paired t test.

These results showed that neuron-derived serum exosomal protein levels of CTSD, LAMP-1, and UBP are increased and HSP70 are decreased in subjects with Alzheimer's disease and are useful for identifying subjects with Alzheimer's disease. These results also showed that neuron-derived serum exosomal levels of CTSD, LAMP-1, and UBP are increased and HSP70 are decreased in subjects as early as 10 years before clinical diagnosis of Alzheimer's disease. These results further showed that assays and methods of the present invention are useful for identifying a subject at risk of a neurodegenerative disorder (e.g., Alzheimer's disease). Additionally, these results showed that the assays and methods of the present invention may be useful for early detection and determining the progression of Alzheimer's disease. These results further indicated that methods and compositions of the present invention are useful for diagnosing Alzheimer's disease and other neurodegenerative disorders.

Example 13: Neuron-Derived Plasma Exosomal Protein Levels in Human Subjects with a Neurodegenerative Disorder Exosomal levels of neuron specific enolase (NSE) and neurofilament light chain (NFL) levels were assayed in human subjects as follows. Thirty milliliters of venous blood were collected from 20 subjects with Alzheimer's disease (AD) and matched control subjects (Alzheimer's Controls—AC). Blood samples were incubated for 10 min at room temperature and centrifuged for 15 min at 1500 g. Plasma was aspirated and stored in aliquots at −80° C.

One-half ml of plasma was incubated with 0.15 ml of thromboplastin-D (Fisher Scientific, Inc., Hanover Park, Ill.) at room temperature for 1 hour, followed by addition of 0.35 ml of calcium- and magnesium-free Dulbecco's balanced salt solution ($DBS^{-2}$) with three-times the suggested final concentrations of protease inhibitor cocktail (Roche Applied Sciences, Inc., Indianapolis, Ind.) and phosphatase inhibitor cocktail (Pierce Halt, Thermo Scientific, Inc., Rockford, Ill.). After centrifugation at 1,500 g for 20 min, supernates were mixed with 252 µl of ExoQuick exosome precipitation solution (EXOQ; System Biosciences, Inc., Mountainview, Calif.), and incubated for 1 hour at 4° C. Resultant exosome suspensions were centrifuged at 1,500 g for 30 min at 4° C. and each pellet was re-suspended in 250 µl of distilled water with inhibitor cocktails by vortex-mixing after a −80° C. freeze-thaw cycle before immunochemical enrichment of exosomes from neural sources.

Each sample was incubated for 1 hour at 4° C. with 1 µg of mouse anti-human CD171 (L1CAM neural adhesion protein) biotinylated antibody (clone 5G3, eBioscience, San Diego, Calif.) in 50 µL of 3% BSA (1:3.33 dilution of Blocker BSA 10% solution in PBS, Thermo Scientific, Inc.) with 50 µL of 3% BSA and incubation for 30 min at 4° C. After centrifugation at 200 g for 10 min at 4° C. and removal of the supernate, each pellet was resuspended in 0.5 ml of M-PER mammalian protein extraction reagent (Thermo Scientific, Inc.), that had been adjusted to pH 8.0 with 1 M Tris-HCl (pH 8.6) and contained the cocktails of protease and phosphatase inhibitors. These suspensions were incubated at 37° C. for 20 min and vortex-mixed for 15 sec before storage at −80° C. until use in ELISAs.

Exosome proteins were quantified by ELISA kits for total neuron-specific enolase (R&D Systems, St. Paul, Minn.), neurofilament light chain protein (NFL) (American Research Products, Waltham, Mass.), and tetraspanning exosome marker human CD81 (Hölzel Diagnostika-Cusabio, Cologne, Germany) with verification of the CD81 antigen standard curve using human purified recombinant CD81 antigen (Origene Technologies, Inc., Rockville, Md.), according to suppliers' directions. The mean value for all determinations of CD81 in each assay group was set at 1.00 and the relative values for each sample used to normalize their recovery.

The statistical significance of differences between group means for cross-sectional patient groups and between each patient group and their respective matched control groups was determined with an unpaired t test including a Bonferroni correction in the interpretation (GraphPad Prism 6, La Jolla, Calif.). Separate discriminant classifier analyses were conducted to define the best simple linear models for comparing group AD with its control group (AC). The discriminant analyses were performed step-wise with the Wilks' Lambda method. In each step, only variables with a minimum partial F of 3.84 to enter and 2.71 to remove were retained. Prior probabilities were considered equal for all groups. Fisher Function Coefficients and within group covariances also were computed. Receiver operating characteristics (ROC) analyses were conducted under the non-parametric distribution assumption for Standard Error of Area to determine the performance of classifier models.

As shown in Table 11 below, neuron-derived serum exosomal NSE and NFL protein levels were significantly increased in subjects with AD compared to their respective control subject serum exosomal levels.

TABLE 11

| Group | NSE (pg/ml) | NFL (pg/ml) |
|---|---|---|
| AD (n = 20) | 6,968 ± 185* | 1,296 ± 62* |
| AC (n = 20) | 3,053 ± 134 | 317 ± 31 |

Mean ± SEM;
*p < 0.0001 compared to Control by paired t test.

These results showed that neuron-derived serum exosomal levels of NSE and NFL protein levels are increased in subjects with AD and are useful for identifying subjects with AD. These results further indicated that methods and compositions of the present invention are useful for diagnosing Alzheimer's disease and other neurodegenerative disorders.

Various modifications of the invention, in addition to those shown and described herein, will become apparent to those skilled in the art from the foregoing description. Such modifications are intended to fall within the scope of the appended claims.

All references cited herein are hereby incorporated by reference herein in their entirety.

What is claimed is:

1. A method of analyzing a sample from a subject comprising the steps of: (i) obtaining a biological sample comprising vesicles from a subject, (ii) isolating vesicles from the biological sample, and (iii) detecting one or more biomarkers from the isolated vesicles, wherein at least one of the one or more biomarkers is selected from the group consisting of Tau, phosphorylated Tau, beta-amyloid 1-42 (Aβ1-42), transactive response DNA binding protein 43 (TDP-43), α-synuclein, superoxide dismutase 1 (SOD-1), FUS RNA binding protein (FUS), FK506 binding protein 51 (FKBP51), insulin receptor substrate 1 (IRS-1), phosphorylated IRS-1, cathepsin D (CTSD), lysosomal-associated membrane protein 1 (LAMP1), ubiquitinylated proteins (UBP), heat-shock protein 70 (HSP70), neuron specific enolase (NSE), and neurofilament light chain (NFL), wherein the biological sample is whole blood, serum, or plasma, and wherein the vesicles are selected from the group consisting of neuron-derived exosomes, astrocyte-derived exosomes, oliogodendrocyte-derived exosomes, and microglia-derived exosomes.

2. The method of claim 1, wherein the detection of one or more biomarkers is the detection of protein, phosphorylated protein, mRNA, or miRNA of the one or more biomarkers.

3. The method of claim 1, wherein the phosphorylated tau and/or phosphorylated IRS-1 is phosphorylated on one or more serine, threonine, or tyrosine residues.

4. The method of claim 1, wherein the phosphorylated tau and/or phosphorylated IRS-1 is phosphorylated at one or more residues selected from the group consisting of Thr-153, Thr-181, Thr-205, Thr-231, Ser-199, Ser-202, Ser-214, Ser-235, Ser-262, Ser-356, Ser-396, Ser-422, Tyr18, Tyr29, Tyr197, Tyr310, Tyr 394, P-S312-IRS-1 and P-panY-IRS-1.

5. The method of claim 1, wherein the isolating vesicles from a biological sample comprises: contacting the biological sample with an agent under conditions wherein a vesicle present in said biological sample binds to said agent to form a vesicle-agent complex; and isolating said vesicle from said vesicle-agent complex to obtain a sample containing said vesicle.

6. The method of claim 1, wherein the subject is selected from the group consisting of a human, a monkey, a dog, a pig, a bovine, a rabbit, a guinea pig, and a rodent.

* * * * *